United States Patent
Baldeschwieler et al.

[11] Patent Number: 5,824,470
[45] Date of Patent: Oct. 20, 1998

[54] METHOD OF PREPARING PROBES FOR SENSING AND MANIPULATING MICROSCOPIC ENVIRONMENTS AND STRUCTURES

[75] Inventors: John D. Baldeschwieler, Pasadena, Calif.; David Randall Baselt, Alexandria, Va.; Marc A. Unger; Stephen D. O'Connor, both of Pasadena, Calif.

[73] Assignee: California Institute of Technology, Pasadena, Calif.

[21] Appl. No.: 453,958

[22] Filed: May 30, 1995

[51] Int. Cl.[6] .................... C12Q 1/68; G01N 33/53; G01N 21/00; C01B 25/00
[52] U.S. Cl. .................... 435/6; 435/7.1; 435/7.2; 422/57; 204/157.45; 204/157.6
[58] Field of Search .................... 435/6, 7.1, 7.2; 204/157.45, 157.6; 422/57

[56] References Cited

U.S. PATENT DOCUMENTS

| | | | |
|---|---|---|---|
| 5,063,081 | 11/1991 | Cozzette et al. | 427/2 |
| 5,242,541 | 9/1993 | Bayer et al. | 156/653 |
| 5,250,473 | 10/1993 | Smits | 437/238 |
| 5,363,697 | 11/1994 | Nakagawa | 73/105 |
| 5,495,109 | 2/1996 | Lyndsay et al. | 250/306 |

OTHER PUBLICATIONS

Lee et al. (1994) Langmuir 10:354–357.
Frisbie et al. (1994) Science 265:2071–2074.
Lee et al. (1994) Science 266:771–773.

*Primary Examiner*—Ardin H. Marschel
*Assistant Examiner*—Jezia Riley
*Attorney, Agent, or Firm*—Swanson & Bratschun LLC

[57] ABSTRACT

Probes for sensing and manipulating microscopic environments and structures, their method of preparation and methods of use are disclosed.

5 Claims, 5 Drawing Sheets

B—∧∧∧∧∧∧∧—X

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 4 amino acid residues
        ( B ) TYPE: amino acids
        ( C ) STRANDEDNESS: single
        ( D ) TOPOLOGY: linear ( x i ) SEQUENCE DESCRIPTION: SEQ ID NO:1:

Tyr Gly Gly Phe ( 2 ) INFORMATION FOR SEQ ID NO:2:

( i ) SEQUENCE CHARACTERISTICS:
        ( A ) LENGTH: 31 amino acid residues
        ( B ) TYPE: amino acids
        ( C ) STRANDEDNESS: single
        ( D ) TOPOLOGY: linear ( x i ) SEQUENCE DESCRIPTION: SEQ ID NO:2:

-continued

```
Tyr  Gly  Gly  Phe  Met  Thr  Ser  Glu  Lys  Ser  Gln  Thr  Pro  Leu
                     5                       10

Val  Thr  Leu  Phe  Lys  Asn  Ala  Ile  Ile  Lys  Asn  Ala  Tyr  Lys
 15                      20                       25

Lys  Gly  Glu
      30
```

( 2 ) INFORMATION FOR SEQ ID NO:3:

( i ) SEQUENCE CHARACTERISTICS:
        ( A ) LENGTH: 8 amino acid residues
        ( B ) TYPE: amino acid
        ( C ) STRANDEDNESS: single
        ( D ) TOPOLOGY: linear ( i x ) FEATURE:
        ( D ) OTHER INFORMATION: Leu at positions 1, 3, 5
            and 7 are D- leucine ( i x ) FEATURE:
        ( D ) OTHER INFORMATION: This peptide is a cyclic
            compound ( x i ) SEQUENCE DESCRIPTION: SEQ ID NO:3:

```
Leu  Glu  Leu  Glu  Leu  Glu  Leu  Glu
                     5
```

METHOD OF PREPARING PROBES FOR SENSING AND MANIPULATING MICROSCOPIC ENVIRONMENTS AND STRUCTURES

FIELD OF THE INVENTION

The present invention relates generally to probes for sensing and manipulating microscopic environments and objects, and more particularly to a chemically functionalized scanning probe tip.

BACKGROUND OF THE INVENTION

Information about the microscopic three dimensional topography of a surface may be obtained by scanning probe microscopy (SPM) techniques providing atomic or near-atomic resolution. The principal scanning probe microscopes are the scanning tunneling microscope (STM) and the atomic force microscope (AFM), both of which achieve the microcharacterization of materials by the use of a fine scanning probe tip. The force or current between the sample atoms and the atoms of the tip is a highly nonlinear function of their relative distance. For surfaces that are nearly atomically flat, the force or current between the sample and the tip is usually dominated by a single atom of the tip that happens to extend slightly more than the others. This property allows imaging of the flat surface with atomic resolution.

The STM operates on electric principles and therefore requires both a conducting tip and a conducting sample. When the tip is positioned within a few atomic diameters of the sample and a bias voltage is applied, a small tunneling current flows between tip and sample. The tip may then be moved laterally with a piezoelectric translator to scan a surface while a computer-controlled feedback mechanism adjusts the height of the tip to maintain a constant current (constant-current mode), or the tip may be moved across the surface at a constant height while monitoring the current (constant-height mode). A surface image may be generated by plotting the tip height or current change versus the lateral position of the tip.

Atomic force microscopy relies upon atomic interactions between the tip and the sample, and has more versatility in that it requires neither a conducting tip nor a conducting sample. In atomic force microscopy, the surface of a sample is scanned by a sharp tip held at the end of an elastic member, such as a wire or cantilever beam, attached at its other end to a transducer. The force between the tip and the sample due to interaction of their electron clouds deforms the elastic member and, if the member is vibrated by the transducer, changes its resonance frequency and amplitude of oscillation. The deformation or vibration is monitored using electron tunneling (using an STM), or laser interferometry, or with an optical lever, and the resulting signal may be used to drive the transducer in a feedback loop. In this manner, the surface topography of the sample may be characterized. The sensitivity of the AFM technique is such that it is also possible to measure the chemical interactions between chemical groups on the probe surface and chemical groups on the sample surface. Thus, it is possible to obtain a chemical interaction image of the sample, which yields information about the chemical nature of the sample surface.

Other scanning probe microscopes, such as magnetic force microscopes and electrostatic force microscopes operate on analogous principles to provide microscopic surface images.

At present, most tips have a tapered shape ending with a rounded surface having a radius of curvature of 5 nm or more. Previously used materials for tips include silicon, silicon nitride, diamond, graphite, transition metal carbides and refractory metals. Such tips may be obtained by one or a combination of methods including cleaving or single crystals, chemical or electrochemical etching, and surface reactions such as anomalous dry oxidation of silicon followed by etching. The radius of curvature and the angle of taper of the tip limit the resolution of imaging of steep or low-radius-of-curvature surface features in the scanning probe microscopes known heretofore, and prevent imaging such features with atomic resolution.

Previous attempts to reduce tip size for improved resolution have focussed on electrochemical etching of traditional tip materials, particularly silicon and tungsten. U.S. Pat. No. 5,242,541, for example, provides a method for producing single-crystal silicon tips with radii of 2 to 5 nm by a masking and etching process. The formation of tungsten tips having radii of curvature as small as 1 to 5 nm by reverse electrochemical etching has also been disclosed (Fontino (1993) Rev. Scientific Instruments 64:159–167). However, etching produces tips with irregular shapes, only some of which are suitable for microscopy. In order to maximize production quality and the resolution of the images obtained by the scanning probes there is still a need for scanning probe tips having regular, predictable shapes, smaller radii of curvature and greater angle of taper than currently available.

There have been few attempts to modify the chemical nature of the probe surface. The non-covalent derivatization of a silicon nitride probe tip by avidin and biotin has been demonstrated. Semi-covalent derivatization of a silicon nitride cantilever by self-assembly of thiols on a sputtered gold surface has also been disclosed. Non-covalent attachment, however, is not sufficient, because the interaction forces between attached molecule and sample are of a comparable strength, and may detach the molecules from the probe surface. The strength of the gold-thiol bond appears nearly sufficient, but the thick layer of gold used reduces the resolution of the probe microscopy technique. Thus, there is a need for a technique which can reliably and stably functionalize probe surfaces.

Heretofore, scanning probe microscopes have been useful for sensing atomic environments. However, the present invention is advantageous in that probes are provided for functions beyond the imaging of microscopic surfaces. For example, tips are provided by the present invention with specific functional moieties to target and/or interact with biological molecules in vivo, or to assist in nano-chemistry, lithography, or nanofabrication techniques.

Accordingly, an object of the present invention is to provide a method of preparing a probe tip functionalized with chemical moieties.

It is another object of the present invention to provide a method of preparing a probe tip suitable for scanning probe microscopy comprising a single macromolecule attached at its apex.

It is a further object of the present invention to provide methods of stiffening appropriate macromolecules, preparing a probe tip to receive a single macromolecule and securing a single macromolecule to a probe tip.

It is a further object of the present invention to provide a method of preparing a probe tip functionalized with a manipulative agent or agents.

It is yet another object of the present invention to provide a method of sensing a microscopic environment using probes prepared by the method described herein.

It is yet another object of the present invention to provide a method of manipulating a microscopic environment, object, or structure using probes prepared by the method described herein.

Additional objects and advantages of the invention will be set forth in the description which follows, and in part will be obvious from the description, or may be learned by the practice of the invention. The objects and advantages of the invention may be realized and obtained by means of the instrumentalities and combinations particularly pointed out in the claims.

SUMMARY OF THE INVENTION

The present invention is directed to methods and apparatus for a probe for sensing and/or manipulating a microscopic environment or structure. For sensing and manipulation techniques that require a probe tip which is entirely functionalized with a specific chemical moiety, the probe tip is prepared using covalent derivatization.

For sensing and manipulation techniques which require attachment of a single macromolecule, the method of preparing the probe comprises the step of protecting an area at the tip of a probe from a passivating agent, where the area is suitable for covalent linkage thereto of a single macromolecule. Preferably, this area is in the range of about 10,000 $Å^2$ to 3 $Å^2$. The tip is then contacted with a passivating agent so that its unprotected portion is passivated. The unpassivated area is then deprotected and one end (the proximal end) of a single macromolecule is covalently attached to the unpassivated area.

For SPM with improved tip radius and aspect ratio, the attached macromolecule preferably has a substantially cylindrical or conical shape and an outer diameter at its distal (unattached) end of about 2 to 50 Å. The probe prepared according to the invention may be used to determine surface topography, or as a chemical or biochemical tool to detect or manipulate molecules or other microscopic substrates.

BRIEF DESCRIPTION OF THE DRAWINGS

The accompanying drawings, which are incorporated in and constitute a part of the specification, schematically illustrate a preferred embodiment of the invention, and together with the general description given above and the detailed description of the preferred embodiment given below, serve to explain the principles of the invention.

DESCRIPTION OF THE PREFERRED EMBODIMENTS

The present invention is directed to a modified scanning probe tip, methods of preparation and methods of use thereof. The invention will be described, in part, in terms of preferred embodiments, as illustrated in the accompanying FIGS.

Figure 1A:
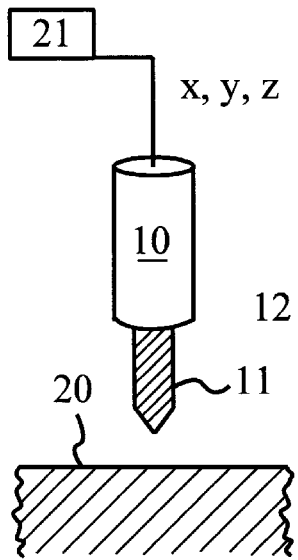
FIG. 1A is a schematic representation of a scanning probe microscope showing the configuration of the piezoelectric tube, tip and sample used for Scanning Tunneling Microscopy.

Referring to FIG. 1A, a piezoelectric tube 10 of a scanning probe microscope equipped with a conventional tip 11, is shown. The tube may be extended in the x 12, y 14 and z 16 directions to support and control the scanning probe tip 11 as it scans over the substrate 20, under control of the computer 21.

Figure 1B:
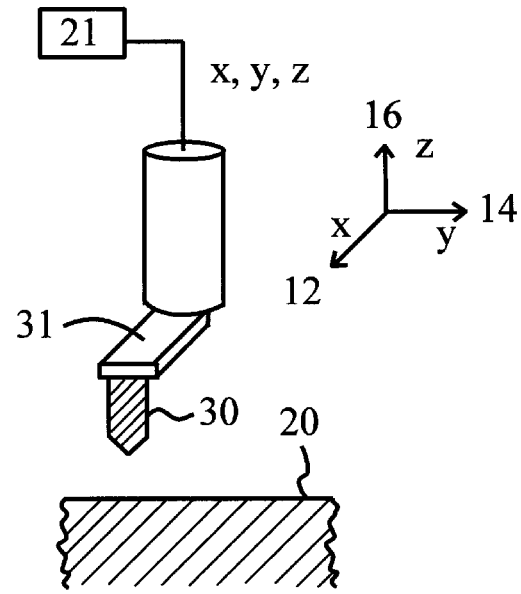
FIG. 1B is a schematic representation of a scanning probe microscope showing the configuration of the piezoelectric tube, cantilever, tip and sample used for Scanning Force Microscopy.

In FIG. 1B, the tip 30 is at the end of a cantilever 31, by which the force on the tip may be measured. The tip 30 may be composed of silicon, silicon nitride, diamond, graphite, transitional metal carbides or refractory metals and sharpened by one or a combination of methods including cleaving of single crystals, chemical or electrochemical etching, ion milling, and surface reactions such as anomalous dry oxidation of silicon followed by etching. The cantilever may be composed of silicon, silicon nitride, diamond, or metal.

Figure 1C:
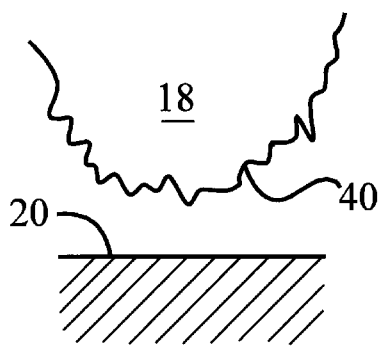
FIG. 1C is an enlarged view of the apex of a typical scanning probe tip 18 known in the art.

FIG. 1C shows an expanded view of the apex 40 of a typical scanning probe tip 18 known in the art. The shape and sharpness of the tip is highly dependent upon the manner in which the tip is prepared.

Functionalization of the scanning probe

Functionalization, as used herein, means the modification of a surface to terminate it with a specific chemical moiety. Depending on the functionalization method, the target moiety may be rigidly determined or freely chosen. If the target moiety may be freely chosen, it will be referred to herein as "Y".

The following are schematic representations (I, II, III, and IV) of the functionalization of the scanning probe tip according to the present invention. In these schemes D represents the reactive group on the substrate; A, B and X are other reactive groups used to form intermediates and Y is the target moiety, the specific chemical moiety which terminates the probe. In schemes II, III and IV, linker molecules are used, typified by the molecule of FIG. 3.

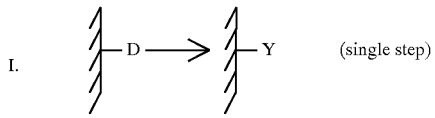

I.                      (single step)

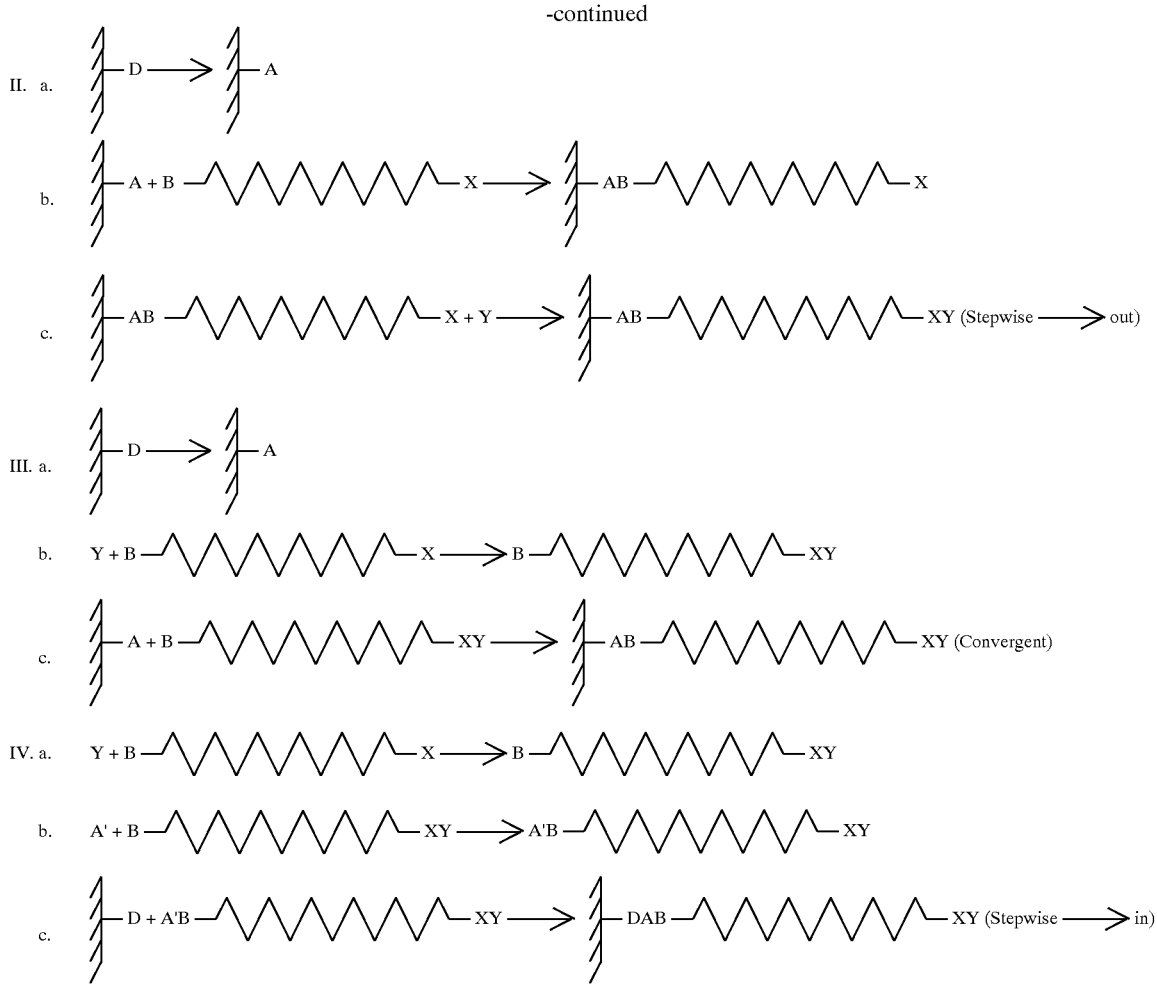

Scheme I shows a direct functionalization from the native reactive moiety on the surface of the probe by conversion in single step to the desired Y moiety. This will be referred to as a "single step" functionalization.

Scheme II is a multi-step conversion from the native probe surface moiety to an intermediate functional group "A" which is, in turn, reacted with a linker terminated at its distal end with a functional group "X". The group "X" is then reacted with the "Y" functional group to form the desired terminus. This will be referred to as a "stepwise out" functionalization.

Scheme III is a multi-step conversion whereby the native functional group of the probe is converted to intermediate function group "A". In a separate step the desired functional terminus "Y" is attached to the end of a linker. The proximal end of the linker containing functional group "B" is then reacted with the surface functional group "A" to attach the linker to the surface. This will be referred to as a "convergent functionalization."

Scheme IV shows the separate synthesis of a functionalizing reagent and its attachment to the probe surface. The functionalizing reagent is synthesized with proximal group A', which directly reacts with surface functional group O, and distal group Y.

The two preferred materials used for the scanning force microscopy probe are silicon nitride ($Si_3N_4$) and silicon (Si). Both of these materials develop a layer of silicon dioxide ($SiO_2$) on exposure to atmospheric oxygen. Silicon dioxide is terminated with silanol groups Si-OH, approximately 1–10 groups/$nm^2$. Table 1 shows the reactions of the silanol groups, indicating their target moieties.

TABLE 1

| Silanol Reactions | | |
|---|---|---|
| >Si—OH + $CH_3Li$ | $\longrightarrow$ | >Si—O—Li + $CH_4$ |
| >Si—OH + ROH | $\rightleftharpoons$ | >Si—OR + $H_2O$ |

TABLE 1-continued

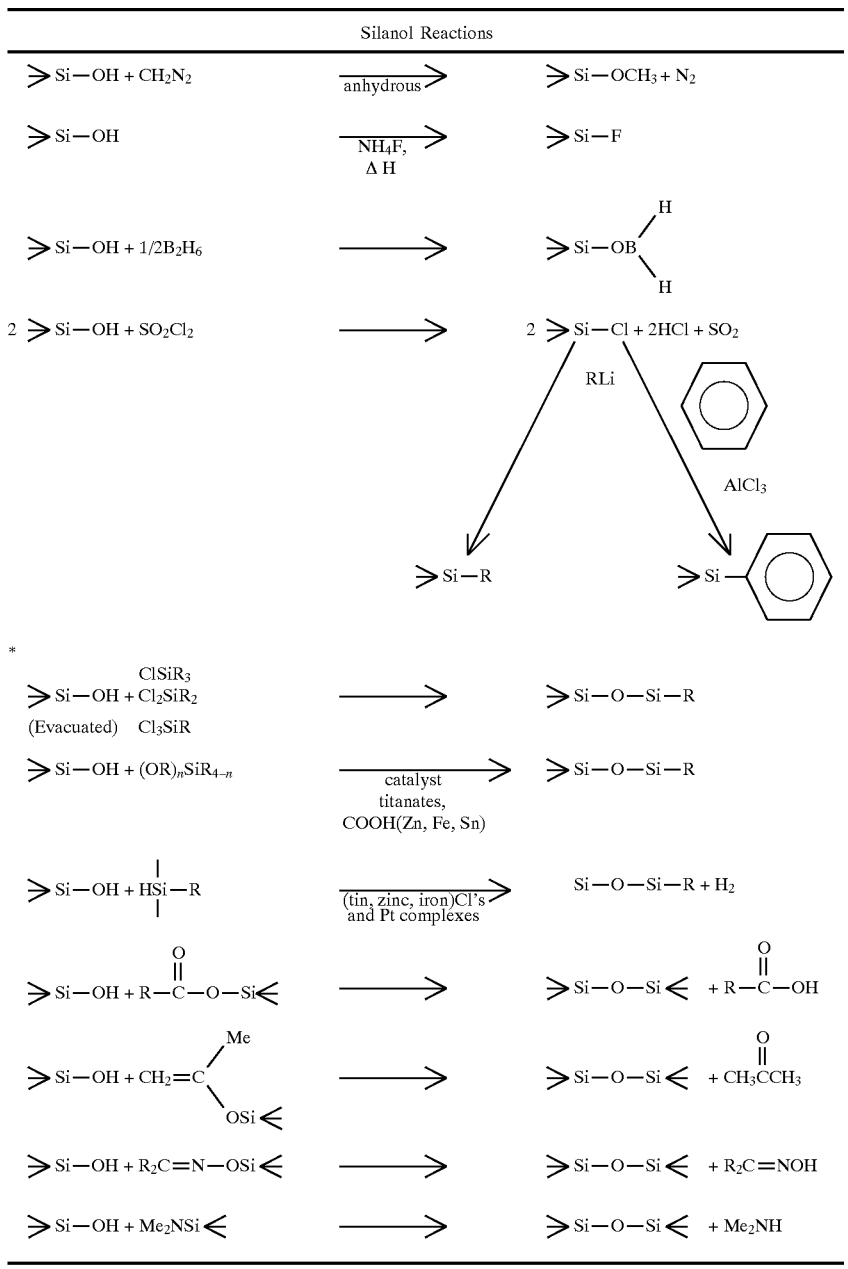

All reactions from * down may be used to attach a more or less arbitrary Y group, assuming the proper synthesis of the derivatizing agent (containing Y).

Figure 2A:
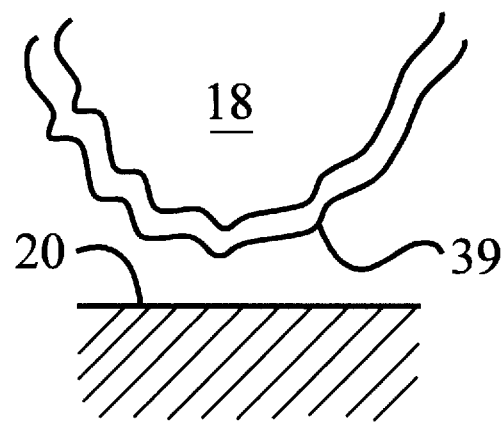
FIG. 2A is an enlarged view of the apex of a scanning probe tip, completely functionalized according to the present invention.

The entire tip may be functionalized to produce a tip as shown in FIG. 2A. The tip 18 is entirely functionalized with layer 39.

The tip may also be functionalized by evaporation of a layer of gold onto the tip surface, followed by treatment with Y-alkyl-thiols, which self-assemble to form a bound Au—S—R—Y monolayer (R=alkyl) on the gold surface. Normally, a Si or $Si_3N_4$ surface is first coated with chromium in order to enhance the adhesion of the gold layer.

Diamond surfaces may be functionalized with fluorine by treatment with fluorocarbons.

Materials used for scanning tunneling microscopy probes must be conductive, and are therefore generally metals or (doped) semiconductors.

Gold and silver may be functionalized by Y-alkyl-thiols, which self-assemble to form a bound Au—S—R—Y monolayer (R=alkyl) on the gold surface.

Aluminum may be functionalized by Y-alkyl phosphates of the class $N(RPO)(OH_2)_nY_{3-n}$. (R=alkyl, n=1–2).

Platinum may be functionalized by treatment with molecules containing an olefinic moiety, i.e. by alkene-Y.

Titanium dioxide ($TiO_2$), tin dioxide ($SnO_2$), and ruthenium dioxide ($RuO_2$) have an oxide coat which allows them to be silanized analogously to $SiO_2$. The surfaces of platinum and gold may be prepared by electrochemical means to have an oxide coat within similar reactivity. In general, any substance with a surface terminated with hydroxyl (—OH) groups may be silanized in like fashion.

EXAMPLE 1

Stepwise-out Functionalization

A silicon scanning probe is functionalized with single-stranded DNA as follows: The surface of the silicon probe is derivatized by immersion in a 2% solution of aminopropyltriethoxysilane (APTS) in anhydrous toluene for 1 hour, yielding an amino (—NH$_2$) group covalently bound to the surface. 10 m g disuccinimidyl suberate (DSS) is dissolved in 600 μL DMSO. A solution of 21 μL aminopentanol in 5.4 mL of 1×PBS buffer is prepared, and the DSS solution is added to it. The resulting solution is stirred for 10 minutes. The probe is added to this solution, and the solution is stirred for 10 minutes. The result is a surface of —OH groups at the end of long spacer arms. This is the starting point for conventional automated solid-phase DNA synthesis. We have replaced the glass beads, which are normally the substrate, with the scanning probe. The scanning probe chip fits easily within a standard DNA synthesis fritted filter chamber.

The functionalization proceeds stepwise, starting from the probe surface and working out, as shown by the following scheme:

EXAMPLE 2

Convergent Functionalization

A silicon nitride scanning probe is functionalized with a peptide epitope sequence as follows: A thin (30 Å) layer of chromium is evaporated onto the probe, followed by a thin (100 Å) layer of gold. A peptide epitope sequence (for instance, enkephalin, Tyr-Gly-Gly-Phe (SEQ ID NO:1), or human endorphin, Tyr-Gly-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-Tyr-Lys-Lys-Gly-Glu (SEQ ID NO:2)) is synthesized using solid-phase Merrifield synthesis such that all amino-containing side chains are protected. The peptide is released from its solid phase support, and treated with a 5 mM solution of Traut's Reagent (2-iminothiolane.HCl), which converts the amino-terminus of the protein to a sulfhydryl terminus. The probe is then added to a 3% solution of this sulfhydryl-derivatized epitope in ethanol and the solution is stirred for 3 hours. The derivatized epitope self-assembles on the gold-coated probe. Finally, the protecting groups on the side-chain amino groups are removed.

As shown in the following scheme both the surface and the target moiety are modified separately, and the two are

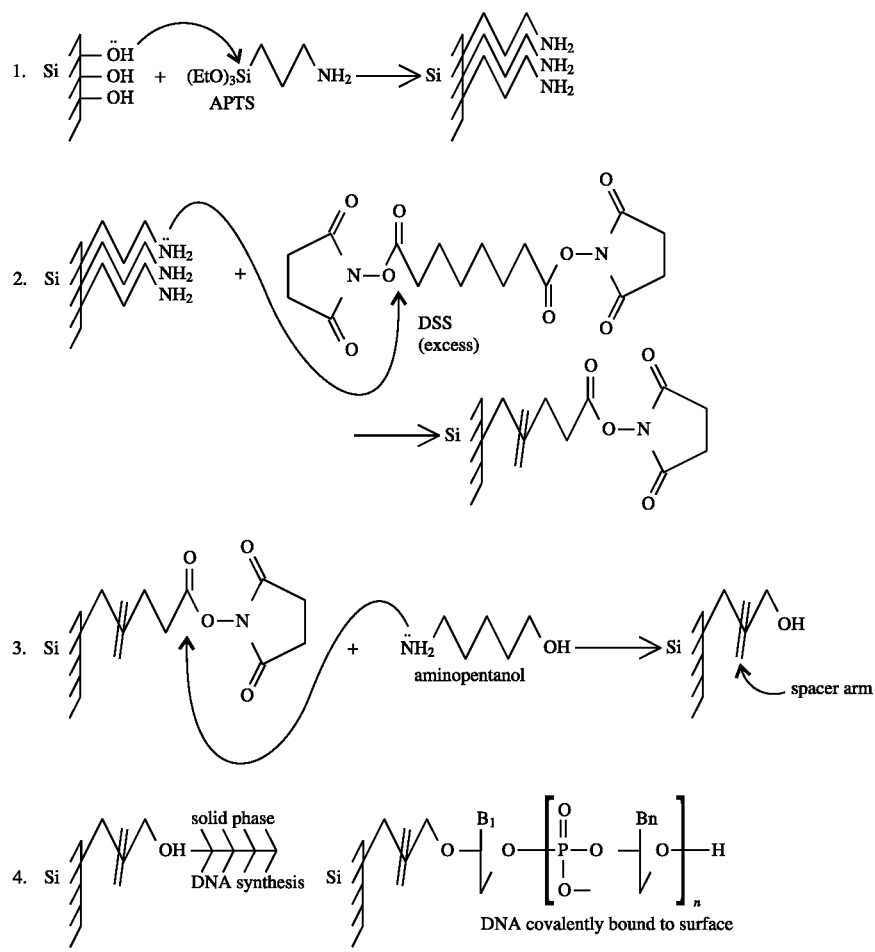

brought together to create the functionalized surface. This is a convergent synthesis.

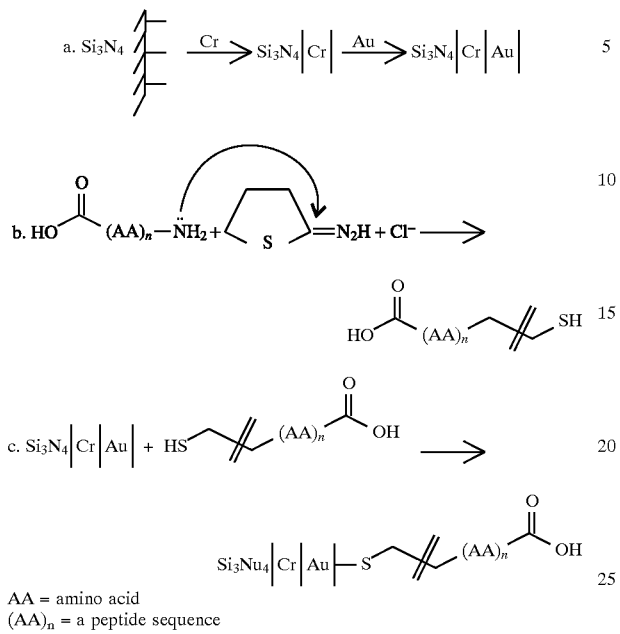

AA = amino acid
(AA)$_n$ = a peptide sequence

EXAMPLE 3

Conduction Through Covalent Bonds

A platinum scanning probe is functionalized with an electroactive reagent (for instance, allylhydroquinone) as follows: the Pt probe is cleaned of organic contaminants by heating in a methane-oxygen flame for 10 minutes with repeated quenching in perchloric acid. Final cleaning is achieved by applying a cyclic potential (2 mV/s, from 0.4 V to 1.3 V, then to −0.4 V and finally to 0.4 V vs NaCe) in 1M HCO$_4$. The probe is then immersed for 5 minutes in a 10 mM solution of the electroactive reagent in pure water.

This functionalized moiety can be oxidized and reduced by application of a potential to the scanning probe, showing that the covalent bonds connecting it to the platinum probe are electrically conductive.

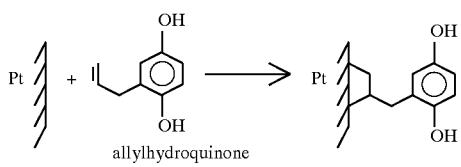

allylhydroquinone

Passivation of the scanning probe

Passivation, as used herein, means the protection by way of a layer on or by chemical, optical, or electric treatment of a substrate surface to isolate the substrate from electrical and chemical conditions in the environment.

Functionalization to a chemically unreactive moiety is one way to implement passivation. Therefore, for tips of silicon and silicon nitride, passivation methods useful in the present invention include treatment with diazomethane, fluorination, chlorination followed by alkylation or arylation, silanization to alkyl groups, hydrosilylation to alkyl groups, or treatment with acloxy-, enoxy-, oxime-, alkoxy-, or alkylamine-organosilanes.

Other means of applying passivation layers include low pressure chemical vapor deposition (LPCVD), as described in U.S. Pat. No. 5,250,473, thermal oxidation, and direct oxidation of the substrate by exposure to oxidizing agents.

EXAMPLE 4

Passivation By Methyl-Functionalization

The surface of a silicon scanning probe may be passivated with methyl groups as follows: the probe is immersed in a 2% solution of trimethylchlorosilane (TMCS) in dry benzene for 1 hour.

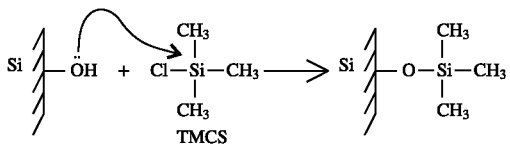

EXAMPLE 5

Passivation by Alkyl-Functionalization

The surface of a platinum scanning probe may be passivated by alkyl-functionalization as follows: the probe is cleaned as described in Example 3, and then functionalized by immersion in a 10 mM solution of 1-octene for 5 minutes.

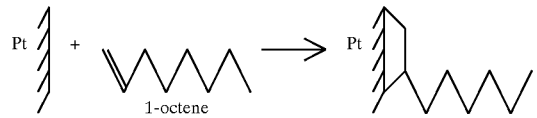

1-octene

Tip-Alpex Functionalization.

The ability to attach a single macromolecule to, or specifically functionalize a small area of, the apex of an SPM tip depends on the ability to physically differentiate the apex from the remainder of the tip, and to cause chemical change based on that differentiation. Since the area is desired to be on the order of molecular dimensions, the physical effects used must be very short-range, capable of affecting one area while leaving another, relatively few atomic distances away, unchanged. There are many ways to do this, including employing steric control, evanescent waves, electron tunneling, or lithographic techniques.

Apex differentiation may constitute either activation toward, or protection from, chemical change.

Methods based on apex activation have three steps:
1. Activation of a small area at the apex of the scanning probe toward functionalization.
2. Functionalization of said area with a desired moiety according to the present invention.
3. Passivation of the non-activated area of said tip according to theneresent invention (if necessary).

Methods based on apex protection have four steps:
1. Protection of a small area at the apex of the scanning probe tip from passivation.
2. Passivation of the unprotected area of said probe tip according to the present invention.
3. Deprotection of the protected area at the apex of said tip.
4. Functionalization of said area with a desired moiety.

Differentiation by Steric Control

Steric interactions (inter-atomic repulsion at short distances) are extremely short range. This type of interaction can be used to block a reagent from the apex of an SPM tip, or to confine a reagent to the apex.

Figure 2B:
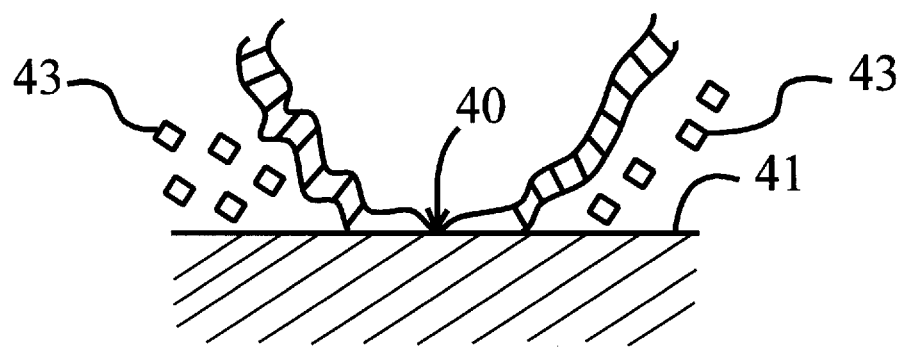
FIG. 2B is an enlarged view of the apex of a scanning probe tip, passivated except for a small area of the apex, as described in the present invention.
Figures 3, 4:
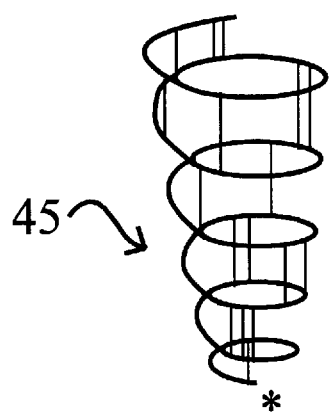
FIG. 3 is a schematic representation of a linker molecule according to the present invention.
FIG. 4 is a schematic representation of a single, rigid macromolecule according to the present invention.
Figure 5:
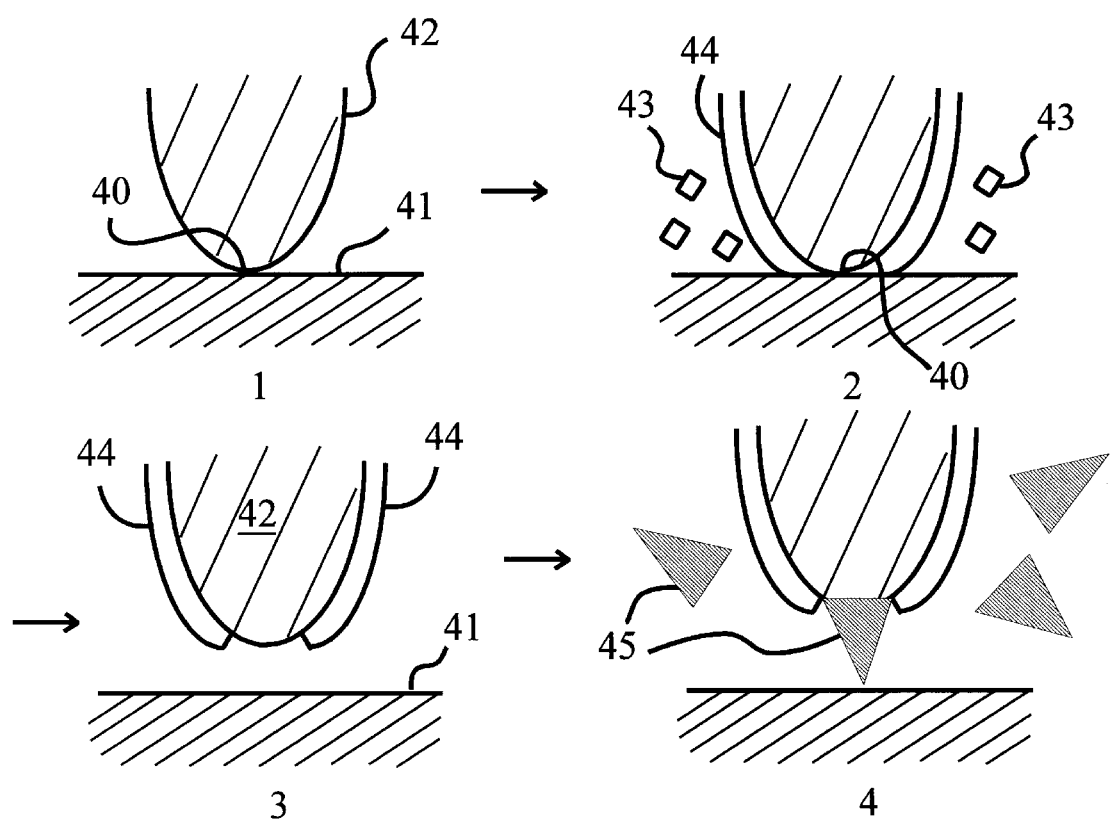
FIG. 5 is a schematic representation of the attachment of a single macromolecule to a scanning probe tip according to the present invention.

Referring to FIG. 5, the protection (1) of a small area 40 at the apex of the scanning probe tip 42 may be accomplished by bringing the small area into close proximity with a substrate surface 41, (2) such that the molecules 43 of the passivating agent are sterically impeded from contact with the small area 40 at the apex of the tip. Passivation layer 44 is formed at other unprotected areas. This can be seen in more detail in FIG. 2B. As an example, if the passivating agent comprises molecules of effective maximum diameter of 20 Å, the apex may be located next to the surface such that the space therebetween is much less than 20 Å. Deprotection (3) is accomplished by simply withdrawing the probe tip 42 from the substrate 41. Functionalization (4) can then proceed using the specialized molecules 45 designed to attach at the unpassivated tip. A typical rigid molecule 45 is shown in FIG. 4.

Differentiate by Applied Potential

Application of an electrical potential between a sharp tip and a substrate creates highly nonhomogeneous electric fields which are extremely intense near the apex of the tip. Magnetic fields at sharp tips are similarly nonhomogeneous and intense at the tip apex. Thus, these fields can be used to guide ions or electrons onto a small area at the apex, to selectively functionalize or passivate the tip. The strong fields may also activate or deactivate chemical groups toward a particular reaction pathway.

Differentiate with Lithographic Techniques

Lithographic techniques to differentiate the tip from other surfaces on the probe depend on lateral, differentiation (along the surface of the probe), rather than vertical differentiation as implied in the evanescent wave and electron tunneling techniques.

Differentiate with an Evanescent Wave

The intensity of an evanescent wave at a flat surface falls off exponentially with distance. A more complicated optical field is created at an aperture smaller than the wavelength of light, with an intensity that may fall off even faster than the evanescent wave at a flat surface. This exponential falloff can be used to differentiate an area at the apex from the remainder of the tip. Since intensity of an evanescent wave decreases exponentially with distance, the probability of reaction of a photoactive group on the probe surface also decreases exponentially with distance from the surface.

Differentiate by Electron Tunneling

The probability of electron tunneling also falls off exponentially with distance. Electro-active (redox) groups on the apex can thus be differentiated by proximity to the substrate. Electron transfer between the electrode and redox-active groups on the probe surface can lead to oxidation or reduction of the redox-active groups. Since electron transfer occurs by quantum-mechanical tunneling, the probability of electron transfer decreases exponentially with distance.

The number of electrons that tunnel may also be controlled by controlling the applied potential and the number of electrons available at the tunneling site.

After the passivation procedure, the small unpassivated area remaining at the apex of the tip is preferably in the range of about 10,000 Å to 3 Å$^2$. It will be realized that the size of area may vary and is controlled by the shape of the tip, and the proximity to and local topography of the substrate surface, or the masking process. However, a small unpassivated area at the substrate tip enhances the probability of attachment thereto of only one macromolecule.

The macromolecule will be attached to the substrate probe tip material in a manner which restricts motion with respect to the substrate. Thus, preferably, there should be a plurality of sites of attachment.

EXAMPLE 6

Apex Assembly of a Single Enzyme Molecule Tip

The apex of a silicon nitride scanning probe may be functionalized with a single molecule of an enzyme (for instance Horseradish Peroxidase, molecule weight 44,000) as follows: A silicon nitride probe is mounted in a SPM liquid cell. The apex of a silicon nitride scanning probe is brought into close proximity with a graphite surface, as described above. The unprotected surface is then passivated by filling the liquid cell with a 2% solution of TMCS in anhydrous toluene and allowing reaction for 1 hour. At the end of this period, the probe tip is withdrawn from the surface and the apex is derivatized by filling the liquid cell with a 2% solution of APTS in anhydrous toluene and allowing reaction for 1 hour. This yields an apex derivatized covalently with amino groups. The probe is then removed from the liquid cell, and the remaining reaction steps are carried out as for functionalization of an entire scanning probe. A solution of 100 mg DSS/1 mL DMSO is prepared, and the scanning probe is stirred in it for 10 minutes. The resulting groups are highly reactive toward amino groups. The probe is removed from the DSS/DMSO solution, rinsed with DMSO to remove excess DSS, and placed in a solution of 3% enzyme in ethanol, where it is allowed to react for 1 hour. Finally, the probe is washed with ethanol and distilled water to remove excess enzyme.

As can be seen from the scheme, the functionalization proceeds stepwise, starting from the probe surface and working out.

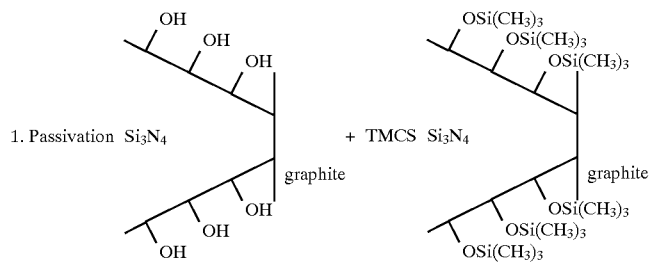

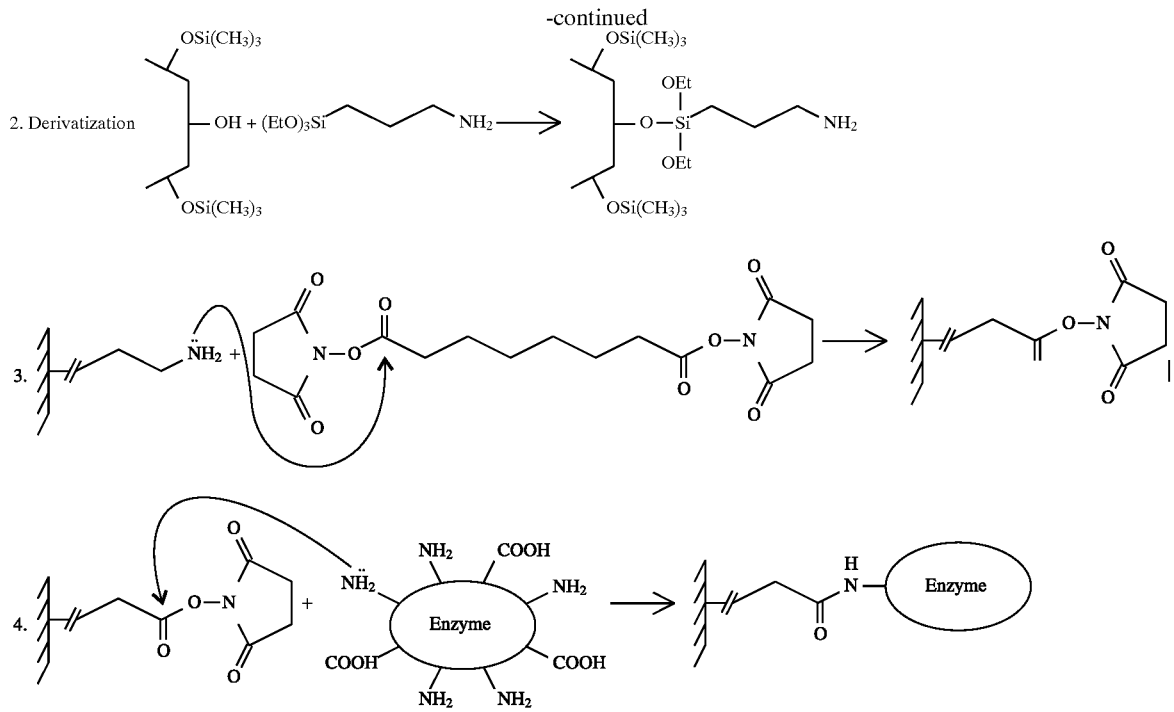

EXAMPLE 7

Apex Assembly of a Polypeptide Nanotubule Tip

A silicon nitride probe is protected with TMCS and its apex derivatized with APTS as described in Example 6. The cyclic polypeptide cyclo[-(D-Leu-Glu-D-Leu-Glu)$_2$] (SEQ ID NO:3) is prepared by the method of Ghadiri et al. (1993) Nature 366:324). Aggregation of this polypeptide is stabilized axially by hydrogen bonds between backbone units and potentially by Van der Waals interactions between the isoleucine side groups. In contrast to the polypeptide of Ghadiri et al., however, lateral association is discouraged, both because of the steric bulk of the isoleucine side groups and because no amino side chains are present to form hydrogen bonds. Self-assembly occurs as pH is reduced.

A single polypeptide nanotube is anchored to the amino apex covalently as follows: a 10 mM solution 1-ethyl-3-(3-dimethylaminopropyl)-carbodiimide hydrochloride (EDC) in aqueous buffer at pH 7 is prepared. 1% by weight of polypeptide is added. The EDC activates the carboxylic acid groups of the glutamic acid side chains for attack by amino groups. After dissolution of the peptide, the probe chip is added and allowed to react for 1 hour. The amino groups on the apex form amide bonds with a polypeptide, anchoring it to the surface. The probe is washed with aqueous buffer solution at pH 9 to remove excess peptide, and then immersed in a fresh solution of 1% polypeptide at pH 7. The pH of the solution is gradually lowered by addition of dilute HCl to allow the polypeptide nanotubule to self-assemble.

As may be seen from the scheme, both the surface and the target are modified separately and then brought together to create the functionalized apex. This is a convergent synthesis.

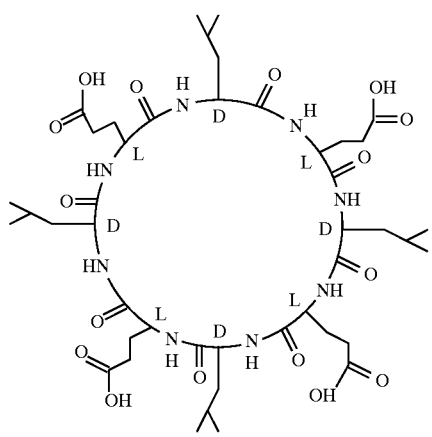

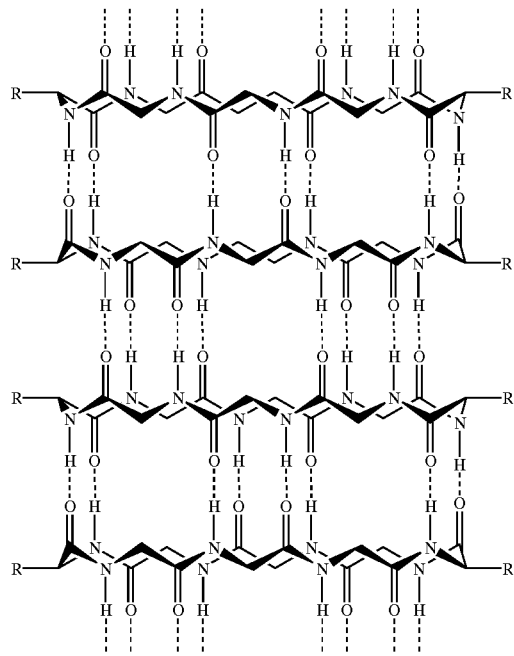
-continued
Adapted from Nature, V366, p. 324
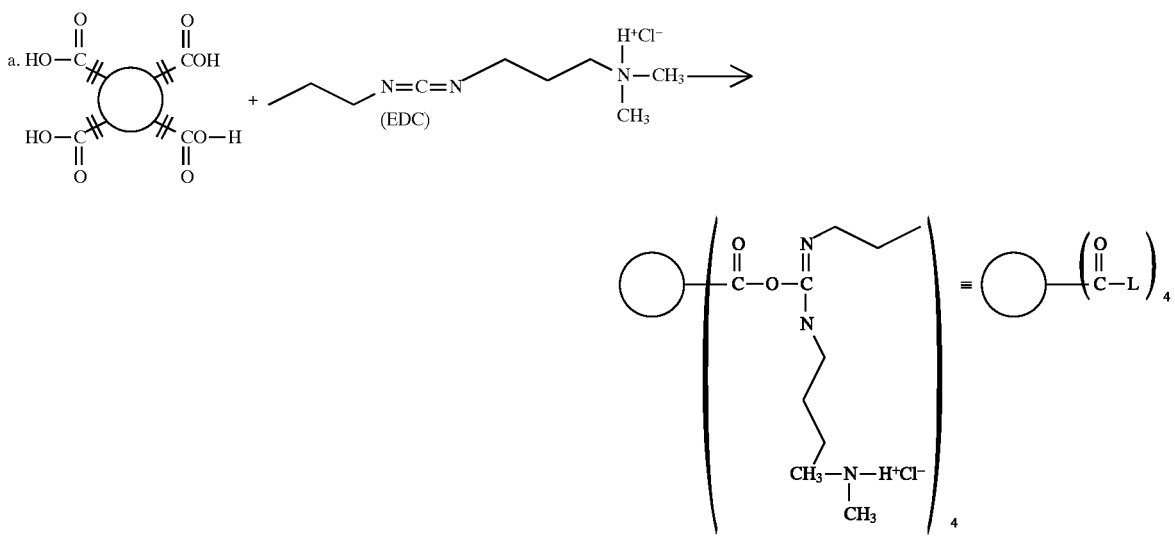
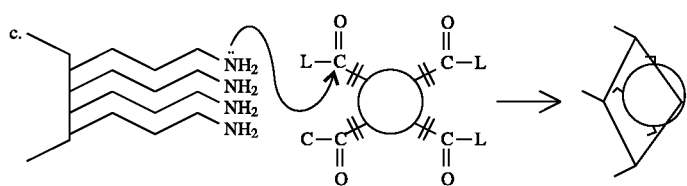

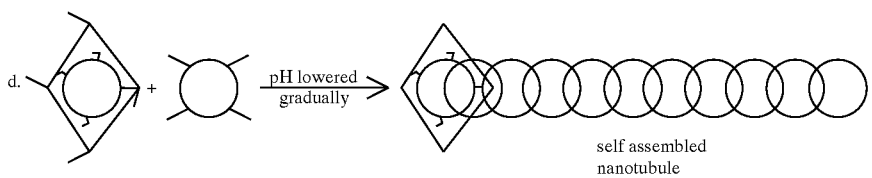

self assembled nanotubule

EXAMPLE 8

Apex Assembly of a DNA Double Helix on a Pt Probe

The apex of a platinum scanning probe may be functionalized with a DNA double helix as follows: the probe is cleaned as described in Example 3, and then mounted in an SPM liquid cell. The apex of the probe is brought into close proximity to a mica substrate, as described above. The unprotected surface is then passivated by filling the liquid cell with a 10 mM solution of 1-pentane in anhydrous pentane and allowing reaction for 5 minutes. The liquid cell is flushed with anhydrous pentane, followed by acetonitrile and pure water and then filled with a 10 mM solution of the vinyl-derivatized double helix (prepared as described below) in water. The probe is withdrawn from the surface and allowed to react for 10 minutes, after which the liquid cell is flushed with pure water.

The 2-aminobutyl-1,3-propanediol (ABPD) structure shown in the following scheme replaces a normal DNA base in a strand of DNA. The DMT-protected phosphoramidite based on the ABPD structure (SBPD-PA) is a perfect chemical replacement for a DMT-protected nucleotide phosphoramidite in automated solid-phase synthesis of DNA; it undergoes the same addition, deprotection, capping, and chain extension reactions. The amino-terminated "side chain" of ABPD-PA can also be derivatized, and this is how the DNA double helix will be attached.

A 100 mM solution of ABPD-PA in anhydrous acetonitrile is prepared. To this is added an equal amount of 1M 1-vinyl-2-pyrrolidionone (VPD) in acetonitrile, and the reaction is allowed to proceed for 30 minutes. This terminates the side chain of ABPD-PA with a vinyl group (ABPD-PA-V). The reaction mixture is purified by column chromatography and the ABPD-PA-V fraction is retained.

The desired sequence of DNA and its complement are synthesized by automated solid-phase synthesis. On one strand, additional 3' and 3'+1 residues are inserted; these are ABPD-PA-V. On the complementary strand, additional 5'−1 and 5' residues are added; these are also ABPD-PA-V. This yields a DNA double-helix with four double bonds capable of covalent bond formation with the surface. The complementary strands are hybridized together.

As can be seen from the scheme, the derivatized DNA double-helix is created entirely separately from the surface, and then attached as a final step. The functionalization proceeds stepwise, starting with the ABPD-PA and working in.

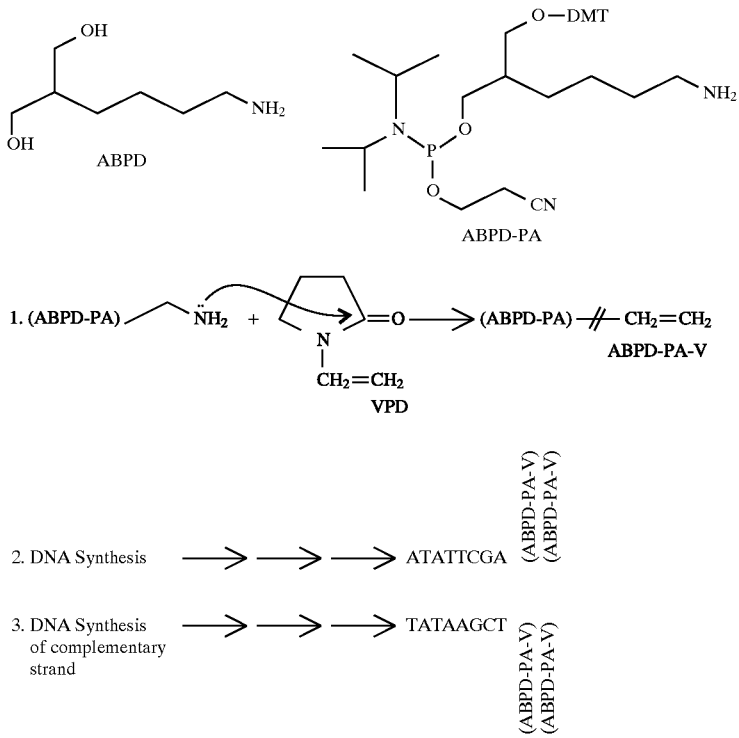

4. Hybridization of complementary strands of DNA →

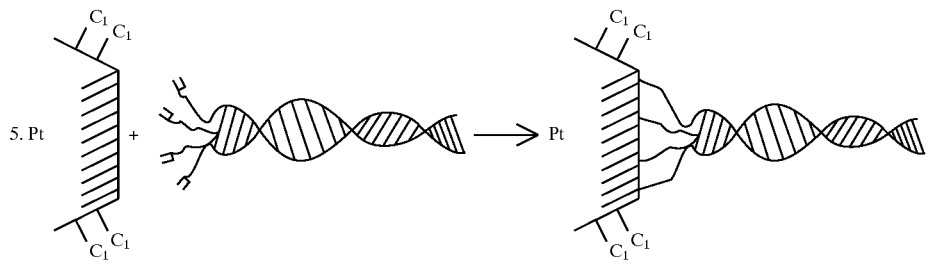

EXAMPLE 9

Differentiation by Steric Control by blocking a passivation reagent from reaching the apex The following steric control methods can be used to constrain a masking agent to the apex.

1. Touch tip apex down on the surface, flow in passivation solution, rinse, retract.

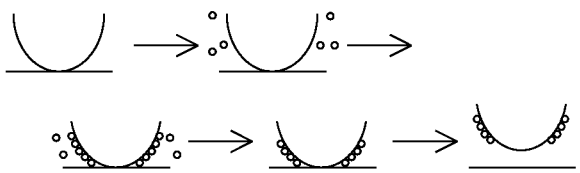

2. Alternatively, touch tip apex down on surface through a drop of passivation solution. Typically, the slow chemical kinetics of passivation prevent apex passivation.

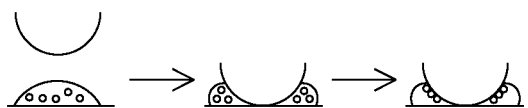

3. Alternatively, touch tip apex on surface through an electroactivatable passivation solution; then
   electroactivate the solution with an external electrode, or
   electroactivate with the tip as an electrode, or
   electroactivate with the substrate as an electrode.
4. Alternatively, touch tip apex down through a heat-activatable passivation solution. Then
   heat solution from the tip, or
   heat solution from the substrate, or
   heat with an external probe, or
   heat with a laser.
4a. Alternatively, touch tip apex down through a light-activatable passivation solution, then, light from tip, substrate, probe, laser etc.
5. Alternatively, touch tip apex down, then electrochemically passivate the tip. Note that this is different than 3. In 3, some species, A, in solution is activated to an activated species A* which can then passivate the surface. In 5, a surface bound species S is oxidized or reduced on the surface of the tip in such a fashion that it can be oxidized or reduced only in the presence of another species present in solution. In 3, A* is blocked from reaching the apex whereas in 5 a necessary solution reagent NN is blocked from reaching S* on the surface.
6. Alternatively touch down the tip apex, then light-passivate tip (same principle as in 5).
7. Alternatively touch down the tip apex, then heat-passivate tip (same principle as in 5).

EXAMPLE 10

Differentiation by steric control to constrain an activation agent to the apex

1. Touch down tip into an aperture filled with an activation reagent/functionalization reagent:

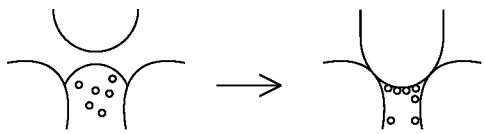

The activation/functionalization reagent may be electroactivated, photoactivated, or heat-activated.

2. In a solution containing electroactivatable reagent, touch down on an aperture where electroactivation, photoactivation or heat activation may selectively occur.

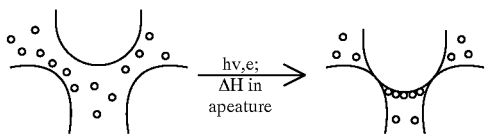

3. Town down on a catalytic surface (for example, to reduce —$NO_2$ groups to —$NH_2$ groups with Pd).
4. Touch down on a surface which chemically reacts with groups on the apex to activate or functionalize the apex.

EXAMPLE 11

Differentiation by steric control to constrain a masking agent to the apex

1. Touch down on a surface to transfer a temporary masking agent to the apex.

EXAMPLE 12

Differentiation by (Evanescent) Photon Control

To photoactivate a reaction (i.e., cause a photochemical change) with light at the apex, one takes advantage of the exponential distance dependence of evanescent waves.

1. Touch tip down at a surface where a wave is undergoing total internal reflection.

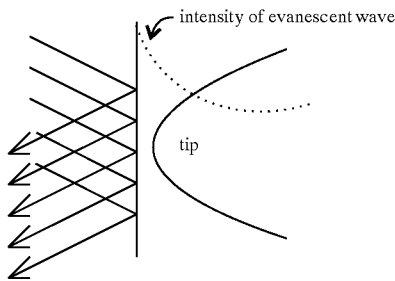

2. Alternatively, touch tip down at an aperture smaller than the wavelength of light.

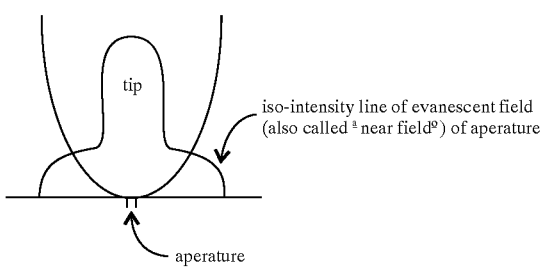

3. Alternatively, the near-field light of a pulled-optical-fiber near-field scanning optical microscope tip (NSOM tip) may be used to photochemically alter the apex of the tip.

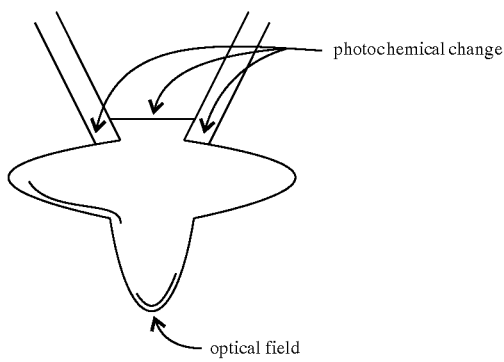

EXAMPLE 13

Differentiation by non-evanescent photon control

1. A tip is brought close to the surface and irradiated with light of high intensity, having a wavelength too long to cause the desired photoreaction. Second harmonic generation at the tip-sample interface will double the frequency (half wave-length) of some of the light. This frequency-doubled light can cause photochemical change which the original light could not, due to higher energy per photon.

2. Alternatively, bring the tip down to a point source of light of the required wavelength to activate
 a frequency-"upping" molecule, or
 an electroactivatable luminescent molecule

EXAMPLE 14

Differentiation by (Tunneling) Electron Control

Specificity of an electrochemical change to the apex comes about through exponential distance dependence of tunneling probability of electrons. For specificity one should limit the number of e⁻ transferred in an electrochemical cell. Therefore, a limited electron source/drain (a "limited e⁻ sink") for this purpose can be provided as follows.

1–6. Either electroactivate groups on apex, with an unlimited e⁻ sink or source, limited e⁻ sink or source or null sink or source, or electroprotect the substrate connected to an unlimited e⁻ sink or source, limited e⁻ sink or source or null sink or source.

7. Connect to sink/source as in 1–6 above, but with the tip in contact, instead of in the tunneling region.

8. Connect to sink/source as in 1–7, but with electron-transfer chemical groups on the substrate.

9. Connect to sink/source as in 8, where the electron-transfer groups are spatially limited.

10. Contact sink where the applied voltage is varied with time.

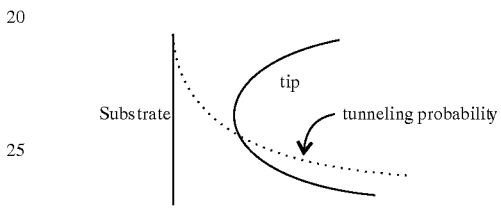

EXAMPLE 15

Limited electron sinks/sources

The following sinks/sources are all drawn with e⁻ transferred from substrate to tip, but the extension to e⁻ transfer from tip to sample is apparent.

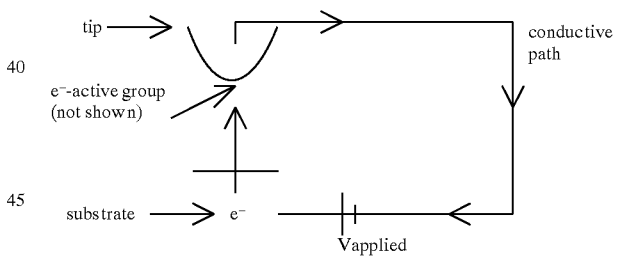

Unlimited Sink
Complete circuit.

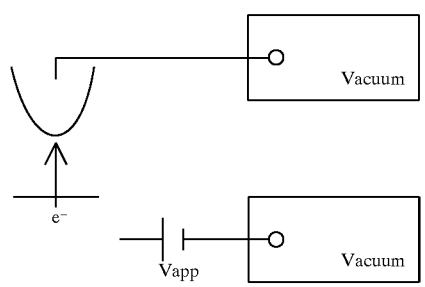

Null sink. Each e⁻ transferred sets up an opposing field.

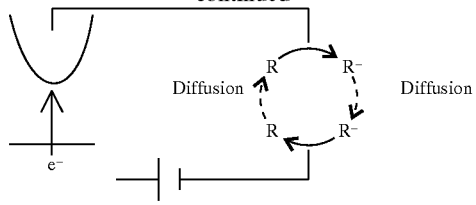

Limited e⁻ sink. Can control the number of e⁻ by limiting the time of contact, since diffusion is slow.

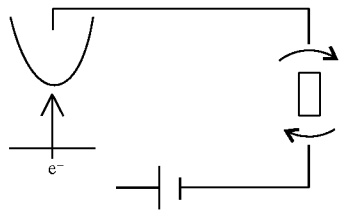

Limited e⁻ sink. Limit limits the number of e amount of A can be limit dilute quantity.

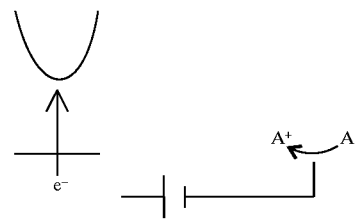

Limited e⁻ sink. As A is converted to A⁺, the concentration of A decreases, the concentration of A⁺ increases and the reverse voltage builds up. By controlling the concentration of A, one should be able to control the number of electrons

EXAMPLE 16

Differentiation by Applied Fields

An applied field is utilized to single out the apex. These are essentially static fields which are not extremely-fast-oscillating fields like an electromagnetic wave (light):

1. A chemical change is induced by field ionization at the apex.
2. A chemical change is induced by high field intensity. For example, if the high field lowers the energy of the transition state of a chemical reaction, ionization is not necessary.
3. As 1., but assisted with applied light or heat.
4. As 2., but assisted with applied light or heat.
5. Chemical change is induced by ion or e⁻ collision, where the ions or e⁻ are guided to the apex by an applied field.
6. Ionize the apex with a field, then guide ions to apex.

EXAMPLE 17

Differentiation by Lithographic Techniques

1. A (negative) resist is applied, the apex exposed with light or e⁻, and unexposed resist is removed. The tip is passivated, the exposed apex resist is removed, and the exposed surface is functionalized.

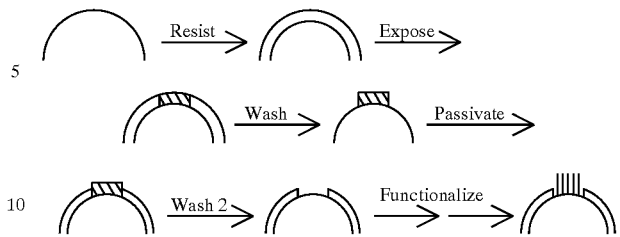

2. A (negative) resist is applied, patterned with light or e⁻, and the unexposed resist is removed. The exposed apex surface is functionalized, and the exposed resist is removed.

3. Alternatively, proceed as 1, but with a positive resist and expose the tip except for the apex.
4. Alternatively, proceed as 2, but with a positive resist and expose the tip except for the apex.
5. Alternatively, proceed as 2 and 3, but with a negative resist of electro- or photo-sensitive molecules which on exposure react to leave the exposed area derivatizable.
6. Alternatively, functionalize entire tip with photo- or electrosensitive target molecule. Irradiate all areas except for apex to remove the target molecule from all sites except the apex.

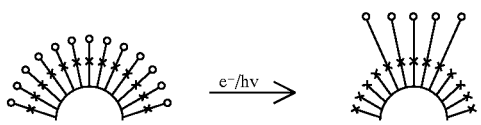

Tip macromolecule

Figure 6:
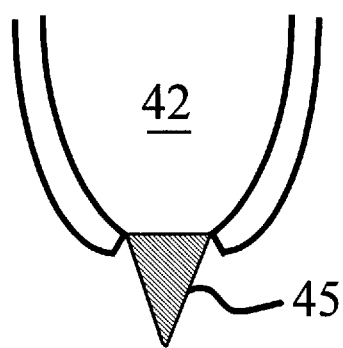
FIG. 6 is a schematic representation of a fully assembled scanning probe tip according to the present invention.

Referring to FIG. 6, the macromolecule 45 needs to be sufficiently rigid after attachment to the tip 42 in order to avoid undesired displacement which is not under control of the computer-controlled mechanism for moving the tip. Hence, complex molecules which are cross-linked, folded or otherwise restricted in degrees of freedom around covalent bonds are required. Such molecules include, but are not limited to, single-wall carbon nanotubes, deoxyribonucleic acid (DNA) double helices, polymeric nanotubes composed of sugar molecules, cyclic peptide nanotubes, proteins, and synthetically constructed macromolecular structures. Nanotubes are molecular structures stacked or coiled to form tubular shapes. Protein structures may be locked by cross-linking or by inserting metal atoms to chelate internal groups.

Single-wall carbon nanotubes having typical diameters of 0.2 to 3 nm may be prepared according to the methods described in Iijima (1993) Nature 363:603 and Bethune (1993) Nature 363:605. These nanotubes are believed to be significantly stiffer than coiled proteins or DNA.

Since a DNA helix fragment is a rigid, electronically coupled aromatic column of stacked base pairs within a sugar phosphate backbone about 2 nm thick which can efficiently promote electron-transfer reactions over distances of more than 40 Å, such helices are useful as probe tips according to the invention.

Polyrotaxane nanotubes, prepared by polymerizing α-cyclodextrin sugar units (see Harada (1993) Nature 364:516) are also useful in the practice of the invention. These tubes have internal and external diameters of about 0.5 and 1.5 nm, respectively. Since cyclodextrins bind organic substrates in aqueous media and the tubes have about the same internal diameter as native biological tubular structures, aside from being useful as a sensing probe, they are useful as extremely selective filters and catalysts for reactions taking place inside the cavity.

Another class of molecules that may be used according to the practice of the invention is cyclic peptide or protein nanotubes having internal diameters of about 0.8 nm (Ghadiri et al. (1993) Nature 366:324). Peptides and proteins may be rigidified with metal atoms, such as copper, which chelate with functional groups internal to the structure. Furthermore, by selecting and/or modifying the amino acid constituents, protein tubes may be prepared to achieve a desired internal diameter or to place reactive moieties at the tip in order to perform particular functions.

The macromolecules, particularly proteins and sugars which have pendant functional groups, can be cross-linked to impart stiffness to the structure. Cross-linking may be accomplished by known methods as disclosed, for example, by Mattson et al. (1993) Molec. Biol. Reports 17:167–183.

Accordingly, the present invention provides a scanning probe tip capable of specific molecular interactions with a substrate. The tip is useful for sensing and analyzing microscopic structures and environments by means of the interactions between the tip moieties and the substrate.

In addition to improving scanning probe microscopy, the functionalized tip of the present invention is useful as a molecular biological or chemical tool. For example, a probe functionalized with a DNA molecule bearing a specific code sequence may be used to selectively detect, manipulate or remove specific DNA fragments in a complex mixture of biological molecules, either in vitro or in vivo. Detection, in this application, may be achieved by monitoring conformational or other changes in the tip molecule caused by binding to its substrate, or by chemical means upon removal of the tip from the mixture, or by means of the force exerted on the tip when it is moved away from the location of the complementary DNA on the substrate.

Similarly, a probe may be functionalized with a protein macromolecule with an epitope sequence at its tip. Such a probe may then be used, in vitro or in vivo to detect, select or manipulate antigenic materials in mixtures.

Referring to FIG. 6, the completed tip comprises a single, rigid macromolecule 45 rigidly attached to a small area of the apex of a scanning probe tip 42.

Accordingly, the present invention provides a scanning probe tip having a smaller radius of curvature, greater angle of taper and a more reproducible shape than the tips previously available. This tip is useful for sensing microscopic environments since the macromolecular tip is able to penetrate or sense finer indentations in a substrate surface than prior tips.

A probe modified according to the present invention may also be used as a tool in nanofabrication techniques, in molecular chemistry or biochemical catalysis. With the appropriate functional group attached, a probe may be used to add or remove a chemical moiety in a precise location on a molecular structure. Alternatively, a probe may act as a catalyst in chemical or biochemical reactions by precise positioning of a specific functional group in the reaction environment, or by providing the reaction environment itself, for instance, the cavity of a tubular macromolecular tip.

The present invention has been described, in part, in terms of preferred embodiments. The invention, however, is not limited to the embodiments depicted and described. Rather the scope of the invention is defined by the appended claims.

What is claimed is:

1. A method of preparing a probe for sensing or manipulating a microscopic environment or structure comprising the steps of:

(a) protecting a small area at the tip of the probe, wherein said area of protection is in the range of about 10,000 $Å^2$ to 3 $Å^2$;

(b) passivating the unprotected area of said probe tip;

(c) deprotecting the protected area of said probe tip; and (d) functionalizing the deprotected area at the tip of said probe with a desired moiety.

2. A method of preparing a probe for sensing or manipulating a microscopic environment or structure comprising the steps of:

(a) activating a small area at the tip of the probe towards functionalization;

(b) functionalizing said area with a desired moiety, comprising a single, rigid macromolecule that has an outer distal diameter in the range of about 2 Å to about 50 Å; and (c) passivating the non-activated area of said tip (if necessary).

3. The method according to claim 2 wherein said single, rigid macromolecule is selected from the group consisting of a carbon nanotube and a polyrotaxane.

4. A method of preparing a probe for sensing or manipulating a microscopic environment or structure comprising the steps of:

(a) protecting a small area at the tip of the probe;

(b) passivating the unprotected area of said probe tip;

(c) deprotecting the protected area of said probe tip; and (d) functionalizing the deprotected area at the tip of said probe with a desired moiety comprising a single, rigid macromolecule that has an outer distal diameter in the range of about 2 Å to about 50 Å.

5. The method according to claim 4 wherein said single, rigid macromolecule is selected from the group consisting of a carbon nanotube and a polyrotaxane.

\* \* \* \* \*